United States Patent [19]

Crowley

[11] Patent Number: 4,799,928

[45] Date of Patent: Jan. 24, 1989

[54] UROLOGICAL DEVICE

[75] Inventor: Ivan P. Crowley, Cape Province, South Africa

[73] Assignee: Femlib Medical Devices (Proprietary) Limited, East London, South Africa

[21] Appl. No.: 1,511

[22] Filed: Dec. 3, 1986

[30] Foreign Application Priority Data

Dec. 6, 1985 [ZA] South Africa .................. 85/9367

[51] Int. Cl.⁴ .............................................. A61F 5/44
[52] U.S. Cl. ..................................... 604/329; 604/317
[58] Field of Search .................................. 604/327–331, 604/317–321, 346–348, 354, 355; 128/760, 761, 767; 4/144.1–144.4

[56] References Cited

U.S. PATENT DOCUMENTS

| | | | |
|---|---|---|---|
| 3,116,734 | 1/1964 | Terman | 604/329 |
| 3,368,914 | 8/1968 | Crowley . | |
| 3,528,423 | 9/1970 | Lee | 604/329 |
| 3,661,155 | 5/1972 | Lindan | 604/329 |
| 3,776,235 | 12/1973 | Ratcliffe et al. | 604/329 |
| 4,200,102 | 4/1980 | Duhamel et al. | 604/331 |
| 4,246,901 | 1/1981 | Michaud | 604/329 |

FOREIGN PATENT DOCUMENTS 2416036 4/1975 Fed. Rep. of Germany ...... 604/329

OTHER PUBLICATIONS

Article from British Journal of Urology—Vol. XLIII No. 4—Aug. 1971, Female Incontinence—A New Approach-Article by Messrs. Crowley, Cardoza & Lawrence.

Primary Examiner—C. Fred Rosenbaum
Assistant Examiner—Mario Costantino
Attorney, Agent, or Firm—Browdy and Neimark

[57] ABSTRACT

An incontinence device for a female user includes a drain tube having a mouth opening, and a vestibulo-vaginal insert extending upwardly from the rear of the mouth opening. The insert is of resilient flexible material expansible laterally in use within the vagina of the user, away from a medial plane. This ensures that the mouth opening of the drain tube is held in register with the urethral meatus of the user.

7 Claims, 3 Drawing Sheets

UROLOGICAL DEVICE

BACKGROUND TO THE INVENTION

This invention relates to a urological device. In particular it relates to an incontinence device for use by an incontinent female.

An incontinence device previously used includes a tubular vestibulo-vaginal insert and a suction disc around the one end of a drain tube which in use is held in position against the urethral meatus of the wearer to permit drainage of urine into the drain tube.

A disadvantage of this previously known device was that it did not fit all wearers equally well. In particular it was found that women who had borne children required additional means to keep the device effectively in position.

It is an object of this invention to provide a device of this kind which can be applied to fit different women effectively.

SUMMARY OF THE INVENTION

According to the invention there is provided an incontinence device for a female user, which includes:
 a drain tube having a mouth opening; and
 a tubular vestibulo-vaginal insert extending upwardly from the rear of the mouth opening and being of resiliently flexible material expansible laterally in use within the vagina of the user, away from a medial plane to ensure that the mouth opening of the drain tube is held in register with the urethral meatus of the user.

The vestibulo-vaginal insert, in compressed shape in use, may be substantially of oval cross-section, the drain tube mouth opening being symmetrically disposed about the medical plane. The said insert may comprise a central spine portion adjacent the drain tube mouth opening, and resilient lobe or wing portions on either side of the spine portion. The lobe or wing portions may be foldable inwardly against their inherent resilience to lie against the spine portion, thereby providing the lateral expansibility to hold the drain tube mouth opening in register with the urethral meatus of the user.

The mouth opening may be larger than the drain tube and may be of bell-mouth shape. The mouth opening may be defined by a thin delicate peripheral flange disposed transversely to the wall of the mouth opening. The flange may lie in a concave surface.

The invention extends also to urological apparatus which includes:
 an incontinence device as described;
 a drain vessel adapted to have its interior at sub-atmospheric pressure; and
 an interconnecting tube adapted to interconnect the end of the drain tube remote from the mouth opening, to the interior of the drain vessel.

The drain vessel may be resiliently compressible to provide the sub-atmospheric pressure inside, upon release. The drain vessel may have securing means for securing it to the body or clothing of the user.

The invention will now be described by way of example with reference to the accompanying diagrammatic drawings.

Figure 1:
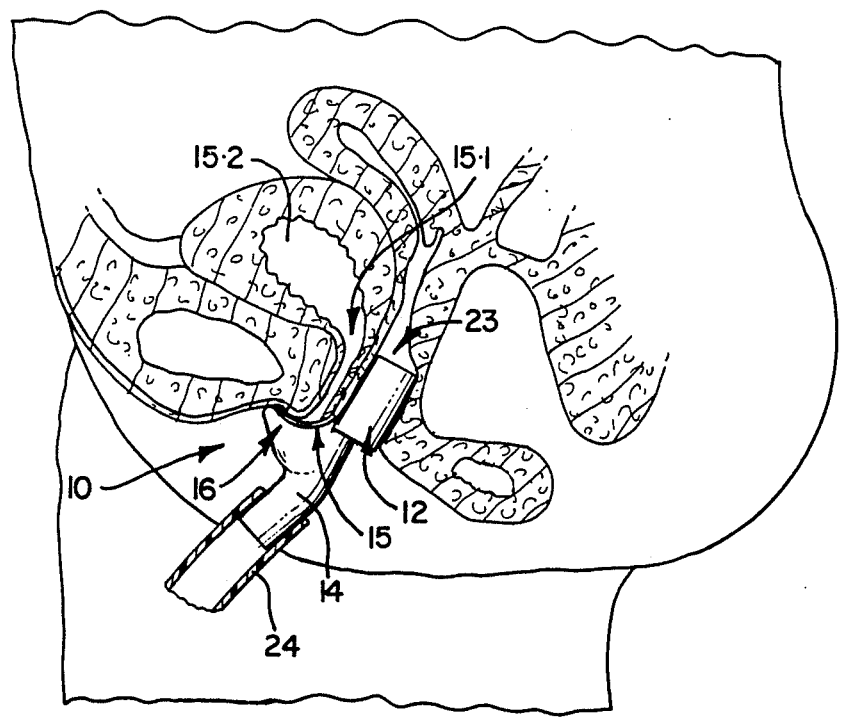
FIG. 1 shows a side elevation of an incontinence device in accordance with the invention, in position for use by a user.

Referring to the drawings, reference numeral 10 refers generally to an incontinence device in accordance with the invention. It includes a vestibulo-vaginal insert 12, and a drain tube 14 having a mouth opening 16 defined by a delicate peripheral flange 17. The insert 12 is of resiliently flexible material and extends upwardly from the rear of the mouth opening 16. The mouth opening 16 is covered by gauze netting 16.1 which is provided to prevent oedema of the periurethral area. The flange 17 is slightly proud of the gauze netting 16.1.

The vestibulo-vaginal insert 12 includes a tubular portion 18 and resilient lobe or wing portions 20 which are of substantially tubular-semi-circular section.

Figure 2:
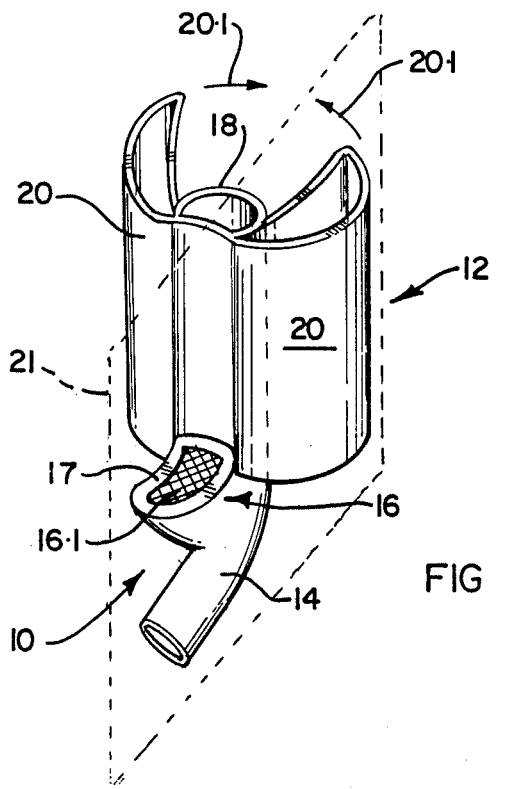
FIG. 2 shows an oblique three-dimensional front view of the device of FIG. 1.
Figure 3:
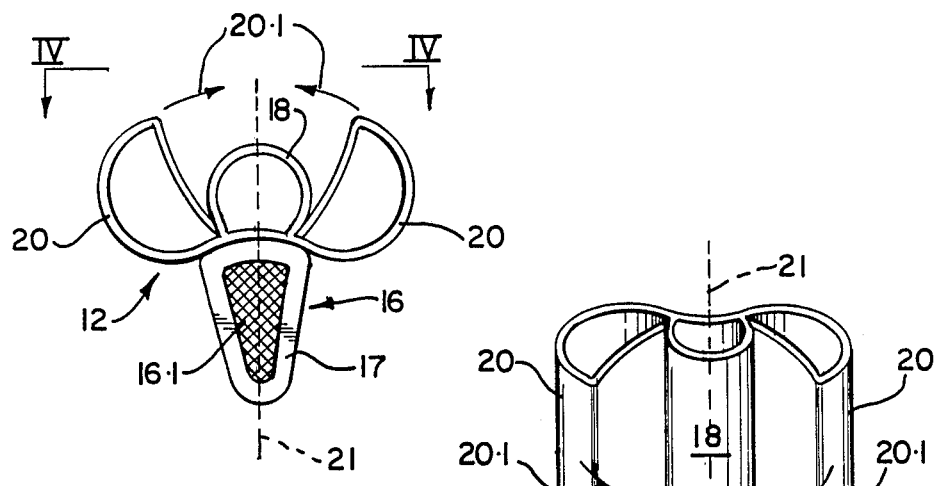
FIG. 3 shows a plan view of the device of FIGS. 1 and 2.
Figure 4:
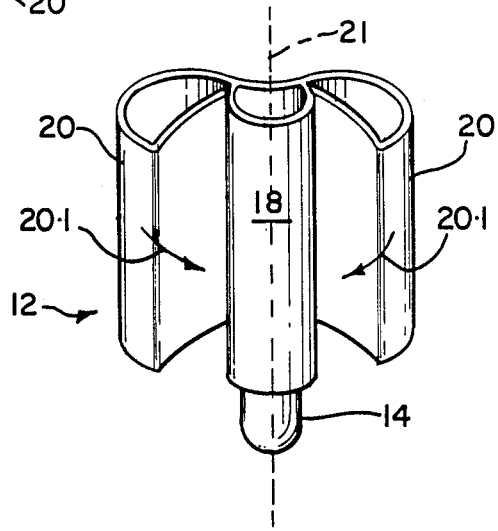
FIG. 4 shows a three-dimensional rear view, generally at IV-IV in FIG. 3.
Figure 5:
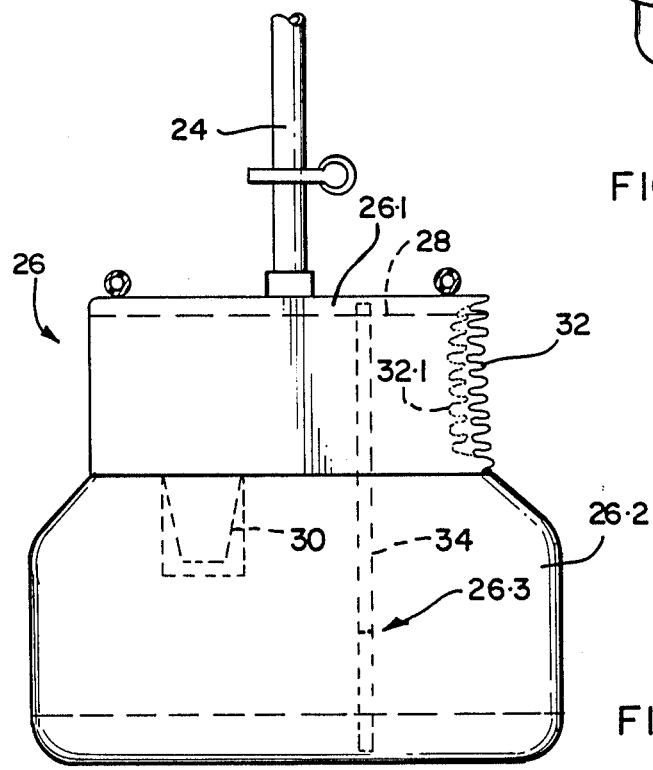
FIG. 5 shows a side view of one type of drain vessel for providing an interior at sub-atmospheric pressure.

In use, the resilient lobe or wing portions 20 of the vestibulo-vaginal insert 12 are compressed into a substantially oval shape by urging them in the direction of arrows 20.1 (see FIG. 2). Thereupon, the insert 12 is inserted in its compressed shape into the vagina 23 of a user, as shown in FIG. 1 of the drawings. There the resilient lobe or wing portions 20 expand laterally on either side of a medial plane 21 until the insert is held securely inside the vagina of the user.

When the device is in position, the flange 17 around the mouth opening 16 seats sealingly around the urethral meatus 15 of the user. The urethra 15.1 leads from the bladder 15.2 of the user. The drain pipe 14 has a flexible interconnecting pipe 24 connecting the end of the drain tube remote from the mouth opening, to an evacuating chamber 26 having sub-atmospheric pressure in the space 26.1 inside it, above the level 28 of the liquid inside the chamber 26.

The chamber 26 has a collapsible tubular (leafed) valve 30 which controls the level 28 of the liquid inside the reservoir 26. The degree of suction exerted on the flange 17 is indicated by the height of the level 28 of the liquid inside the chamber 26 at any given moment.

The chamber 26 has a flexible wall 32 which, by flexing, to a position 32.1 (say) also serves as an indication of the degree of sub-atmospheric pressure which is present inside the space 26.1, and also compensates for any tendency to temporary overfilling. The difference between the atmospheric pressure and the pressure inside the space 26.1 is the pressure which operates to urge the flange 17 to seat sealingly around the urethral meatus 15.

The chamber 26 may be compressed to discharge contained gas (air) into the lower part via the valve 30 or via the tube 34. When the chamber 26 is now released, liquid is aspirated up the tube 34 to prime the chamber. The lower part 26.2 of the chamber acts as a drain vessel, and is open to atmosphere. The height 26.3 to which the liquid rises inside the tube 34 is an indication of the degree of sub-atmospheric pressure in the space 26.1.

Figure 6:
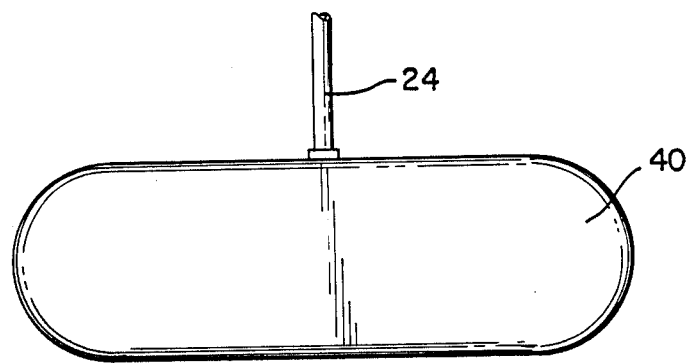
FIG. 6 shows a side view of another type of drain vessel.
Figure 7:
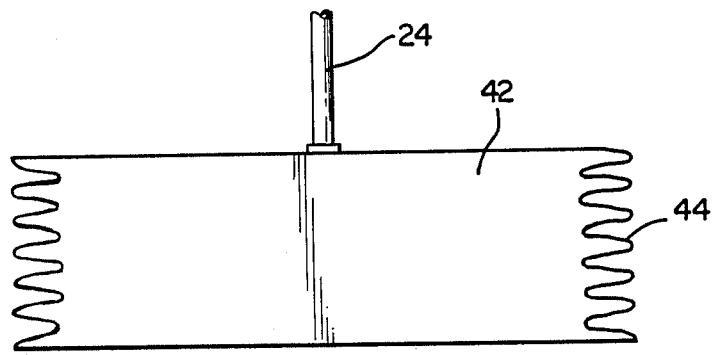
FIG. 7 shows a side view of yet another type of drain vessel.
Figure 8:
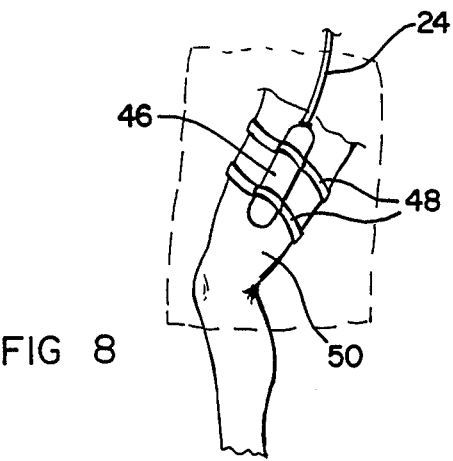
FIG. 8 shows a side view of yet another type of drain vessel, strapped in position on the inner thigh of a user.

Referring now to FIGS. 6 to 8 of the drawings, there are shown different types of evacuating chambers 40, 42 which has bellows sides 44, and a chamber 46 which has straps 48 for strapping to the thigh 50 of a user. These chambers 40, 42 and 46 enable the user to be mobile. When these chambers 40, 42 and 46 are used the periurethral area around the urethral meatus 15 is subjected to slight suction developed by expelling the contained gas (air) from the chambers 40, 42, and 46, by squeezing and releasing the said chambers.

The tubular portion 18 of the insert 12 also serves in practice to drain menstrual or other secretions from the vagina 23 while the device is used.

I claim

1. An incontinence device for a female user, which includes
   a drian tube having a mouth opening defined by the inner periphery of a thin delicate peripheral flange disposed transversely to the wall of the mouth opening, the flange being shaped to seat sealingly around the urethral meatus of a user; and
   a vestibulo-vaginal insert extending away from the drain tube and being of resiliently flexible material expansible laterally in use within the vagina of the user, away from a medial plane to ensure that the mouth opening of the drain tube is held in register with the urethral meatus of the user, the vestibulo-vaginal insert comprising a central spine portion adjacent the drain tube mouth opening, and resilient lobe or wing portions of generally semi-circular section on either side of the spine portion, the lobe or wing portions being foldable in use inwardly from a relaxed shape against their inherent resilience to lie in laterally compressed shape against the spine portion, thereby providing the lateral expansibility to hold the drain tube mouth opening in register with the urethral meatus of the user.

2. A device as claimed in claim 1, in which the flange is shaped to lie in a concave surface, the drain tube mouth opening being larger than the drain tube and being symmetrically disposed about the medial plane.

3. A device as claimed in claim 1, in which the spine portion and the lobe or wing portions are of cylindrical tubular form, the connection of the lobe or wing portions to the spine portion extending longitudinally along the spine portion from a position adjacent the drain tube, and the insert having a larger dimension laterally transverse to the medical plane than in a direction parallel thereto.

4. A device as claimed in claim 3, in which the insert when in laterally compressed shape with the wing portions folded inwardly against the spine portion is of generally oval cross-section, such compressed shape of the insert corresponding to its shape when it is in use inside a vagina, the major axis of the oval in use being disposed transversely to the medical plane of the user.

5. A device of claimed in claim 1, in which gauze netting is provided across the mouth opening at a level slightly lower than the peripheral flange.

6. Apparatus which includes:
   an incontinence device as claimed in claim 5;
   a drain vessel having suction means for placing its interior under slight sub-atmospheric pressure; and
   an interconnecting tube for interconnecting the end of the drain tube remote from the mouth opening, to the interior of the drain vessel.

7. Apparatus as claimed in claim 6, in which the drain vessel is compressible and has securing means for securing to the body or clothing of a user.

* * * * *